(12) United States Patent
Hahn (10) Patent No.: US 6,321,118 B1
(45) Date of Patent: Nov. 20, 2001

(54) METHOD AND APPARATUS FOR POWER LINK DETECTION WITH IMPLANTABLE MEDICAL DEVICES

(75) Inventor: Tae Whan Hahn, Northridge, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/492,735

(22) Filed: Jan. 27, 2000

Related U.S. Application Data
(60) Provisional application No. 60/117,885, filed on Jan. 28, 1999.

(51) Int. Cl.[7] .................................................. A61N 1/378
(52) U.S. Cl. .................................................. 607/61
(58) Field of Search .................................. 607/32, 33, 55, 607/56, 57, 61

(56) References Cited

U.S. PATENT DOCUMENTS

| | | | |
|---|---|---|---|
| 4,223,679 | 9/1980 | Schulman et al. | 128/419 |
| 5,117,825 | 6/1992 | Grevious | 128/419 |
| 5,314,453 | 5/1994 | Jeutter | 607/61 |
| 5,383,912 | 1/1995 | Cox et al. | 607/32 |
| 5,411,536 | 5/1995 | Armstrong | 607/32 |
| 5,438,990 | 8/1995 | Wahlstrand et al. | 128/653.1 |
| 5,569,307 | 10/1996 | Schulman et al. | 607/56 |
| 5,630,836 | 5/1997 | Prem et al. | 607/61 |
| 5,674,265 | 10/1997 | Deschamps et al. | 607/60 |
| 6,212,431 | * 4/2001 | Hahn et al. . | |

* cited by examiner

Primary Examiner—Scott M. Getzow
(74) Attorney, Agent, or Firm—Bryant R. Gold (57) ABSTRACT

A dual directional coupler is placed in the forward power-delivery path of an external transmitter adapted to transmit power to a receiver of an implantable medical device. The dual directional coupler monitors both the forward and reflected (or reverse) power being sent to, and being reflected from, the implantable device. When a valid power link is established between the external transmitter and the implantable medical device, the reflected power falls below a prescribed threshold. When a valid power link does not exist, or when a previously-established power link is broken, then the reflected power rises above the prescribed threshold. The presence of a valid power link is established by monitoring whether the reflected power is above or below the prescribed threshold. The dual directional coupler may be realized using passive discrete circuit components, such as capacitors and inductors; or alternatively using a pair of small transformers, each having a primary and secondary winding wound on a magnetic toroidal core.

16 Claims, 5 Drawing Sheets

METHOD AND APPARATUS FOR POWER LINK DETECTION WITH IMPLANTABLE MEDICAL DEVICES

This application claims the benefit of U.S. Provisional Application Serial No. 60/117,885, filed Jan. 28, 1999, which application is incorporated herein by reference.

BACKGROUND OF THE INVENTION

The present invention relates to implantable medical devices, and more particularly to a method and apparatus for detecting a power link between an external programmer/controller device and an implantable medical device.

In U.S. Pat. No. 5,569,307 there is disclosed an implantable cochlear stimulator (ICS) having back telemetry features. The back telemetry features allow an external wearable processor (WP), inductively linked with the ICS, to receive data and status signals from the ICS. These data and status signals assure that the WP is in proper signal contact with the ICS, and that the ICS is functioning properly. More particularly, as disclosed in the '307 patent, only when a prescribed combination of various status signals within the ICS are present, is a back-telemetry carrier signal and FSK data transmitted to the WP. The back-telemetry carrier signal, when received at the WP, thus acts as a handshake signal to signal the WP that the ICS is in proper signal communication with the WP, and that operation of the ICS can proceed. If the backtelemetry carrier signal is not received by the WP, then the WP does not send the necessary initialization data to the ICS, and operation of the ICS cannot proceed. The '307 patent is incorporated herein by reference.

Unfortunately, detection of the back-telemetry power signal requires appropriate detection circuitry within the external unit. While such detection circuitry may be of any straightforward design, it takes additional components and consumes additional power. Additional componentry and higher power consumption were not significant design considerations for a WP of the type disclosed in the '307 patent because the WP therein disclosed is a belt-worn or pocket-carried device powered with an easy-to-replace battery. However, such is not the case with the newer external units designed to be worn behind the ear. Rather, such behind-the-ear (BTE) units must be both physically small and light weight. Moreover, such BTE units, while ultimately designed, perhaps, for use with more-efficient implantable units, must be backwards compatible. That is, the small, light-weight BTE unit must still provide the operating power and control signals necessary to operate an existing ICS, including an ICS of the type described in the '307 patent. Hence, it is seen that there is a need for power-link detection circuitry within the BTE unit that is able to detect when a valid power link exists between the BTE and the ICS. Such power-link detection circuitry must be much smaller than, and must consume significantly less power than, the detection circuitry that would otherwise have to used to detect a back-telemetry carrier signal.

SUMMARY OF THE INVENTION

The present invention addresses the above and other needs by providing a dual directional coupler in the forward power-delivery path of an external transmitter adapted to transmit power to a receiver of an implantable medical device. The dual directional coupler monitors both the forward and reflected (or reverse) power being sent to, and being reflected from, the implantable device. When a valid power link has been established, the reflected power falls below a prescribed threshold. When a valid power link does not exist, or when a previously-established power link is broken, then the reflected power rises above the prescribed threshold. Thus, the present invention determines whether a valid power link exists by simply monitoring whether the reflected power is above or below the prescribed threshold. Should the reflected power be above the prescribed threshold, then that indicates a proper power link does not exist, or has been lost or broken, and a power link status signal is generated indicating a NO-LINK condition. A NO-LINK condition indicates that appropriate corrective action must be taken. Upon undertaking such corrective action, the reflected power will drop below the prescribed threshold, and the power link status signal will change to a LINK condition. A change from a NO-LINK to a LINK condition in the power link status signal automatically causes reinitializing the implant device by sending a new initialization sequence.

The invention may be characterized as an apparatus that determines whether a power link has been established with an implantable medical device. The apparatus includes: an RF oscillator that generates an RF signal; a headpiece having a transmitting coil; a power amplifier that amplifies the RF signal to produce an RF power signal; an output power path that connects the RF power signal with the transmitting coil; a directional coupler connected in-line with the output power path between the power amplifier and the transmitting coil, the directional coupler having a reflected power port on which a reflected power signal appears having a magnitude proportional to reflected power present on the output power path; and a comparator circuit that compares the reflected power signal to a threshold reference signal and that generates a power link status signal as a function of whether the reflected power signal exceeds the threshold reference signal; wherein the power link status signal provides an indication of whether a power link is established with the implantable medical device.

The present invention may further be characterized as a method of determining whether a power link is established with an implantable medical device. Such method includes the steps of: (a) generating a power signal; (b) transmitting the power signal to the implantable medical device over an output power path; (c) monitoring reflected power present on the output power path; (d) comparing the reflected power to a threshold reference signal; and (e) generating a power link status signal as a function of the comparison performed in step (d).

It is an object of the present invention to provide a method and apparatus for detecting when a valid power link condition exists between a transmitting circuit and a receiving circuit without the need for back-telemetry signals from the receiving circuit.

It is a further object of the invention to provide power-link detection circuitry that consumes very little power, e.g., much less than 1 mW, is very small, and is thus suitable for use in a small, light-weight, battery-operated BTE cochlea-stimulation systems.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

At the outset, it should be noted that while the following description of the invention relates to its use within a cochlea stimulation system, such use of the invention is only exemplary, and not limiting. The invention may be used in any system where a transmitter needs to communicate with a remote receiver (where "remote" means not physically connected to the receiver) and where the receiver does not need to send a backtelemetry handshake signal back to the transmitter to inform the transmitter concerning the status of the received signals. The typical application is where the transmitter and receiver are inductively coupled to each other, each with a coil that needs to be aligned with the other coil in order for an optimum transfer of energy to occur from the transmitting coil to the receiving coil.

Figure 1A:
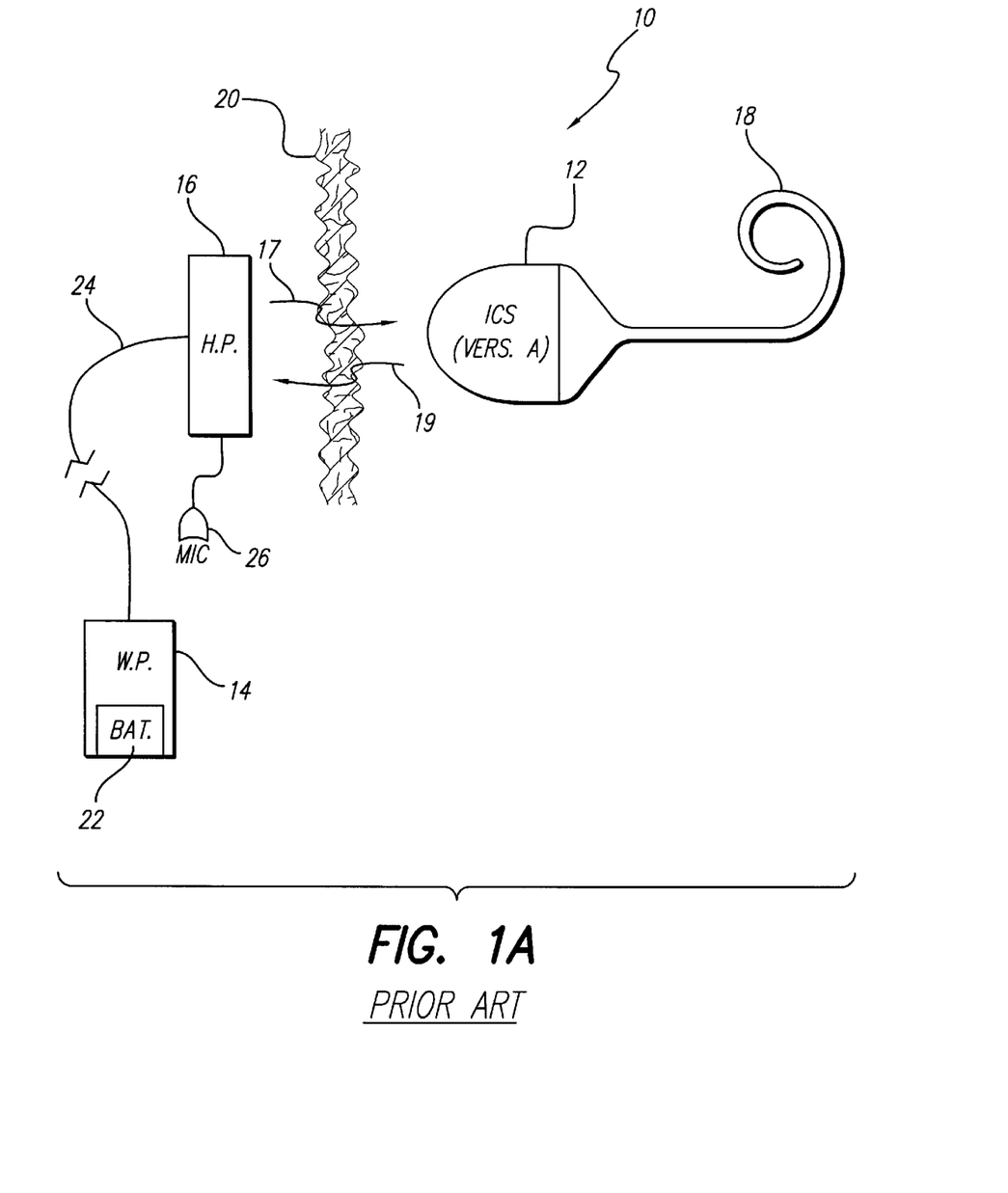
FIG. 1A schematically depicts an implantable cochlear stimulator (ICS) coupled to an external headpiece (HP) and wearable processor (WP)

Turning first to FIG. 1A, there is shown a simplified block diagram of a cochlear stimulation system 10 that uses a first version (version A) of an implanted cochlear stimulator (ICS) 12, an external word processor (WP) 14, and a headpiece (HP) 16. The ICS is implanted underneath the skin 20 of the user, and includes an electrode array 18 that is positioned within the cochlea of a user. The WP 14 includes a replaceable battery 22 that provides operating power for the entire system 10. The WP is connected to the headpiece 16 via a suitable cable 24. Coupled to, or included as an integral part of, the HP 16 is a microphone 26.

The HP 16 further includes, as is known in the art, a transmitting coil and a permanent magnet (not shown in FIG. 1A). The ICS 12 similarly includes a receiving coil and a permanent magnet (not shown). In use, the magnetic attraction between the permanent magnets in the HP and ICS hold the HP is a desired position that roughly aligns the HP coil with the receiving coil. Forward power, e.g., a carrier signal (represented in FIG. 1A as the arrow 17), may then be coupled from the HP to the ICS. For the ICS version used in FIG. 1A, a backtelemetry signal 1 is generated by the ICS, received by the HP 16, and processed by the circuits within the WP 14. Such backtelemetry signal thus provides, e.g., a feedback signal that may be used for many purposes. One purpose is to use the feedback signal as part of a power control loop as disclosed in U.S. Pat. application No. 08/932, 565, filed Sept. 19, 1997, now U.S. Pat. No. 5,876,425, and assigned to the same assignee as is the present application. The '425 patent is incorporated herein by reference. Basically, the power control loop disclosed in the '425 patent uses the backtelemetry signal to let the WP know how much power has actually been received in the ICS, so adjustments may be made, as necessary, to the amount of forward power sent to the ICS is the carrier signal 17.

As previously indicated, detecting and using the backtelemetry signal 19 to monitor the status of the ICS 12 provides a very effective mechanism for determining whether the ICS 12 is functioning properly, and whether the ICS 12 and the HP 16 are in proper alignment. As indicated in the previously referenced '307 patent, one version of the ICS 12 (e.g., version A for purposes of the present application) does not even generate the backtelemetry handshake signal 19 until at least four specific conditions are satisfied within the ICS: (1) a carrier signal must be detected within the ICS, (2) a phase-locked loop used within the ICS must be locked, (3) the power level within the ICS must be above a certain level, and (4) a parity alarm signal associated with the transfer of command data to the ICS must be properly set. When all four of these conditions are met, then the backtelemetry signal 19 is generated, which when received at the HP 16, and processed within the WP 14, triggers the generation of the other command signals that must be sent to the ICS that enable it to operate and carry out its intended function.

In operation, the cochlea stimulation system 10 detects audio sounds through the microphone 26. These sounds are processed within speech processing circuits housed within the WP 14 in accordance with a selected speech processing strategy in order to convert them to appropriate stimulation command signals. The stimulation command signals are then transmitted to the ICS 12 with a carrier signal. Typically, the command signals amplitude modulate the carrier signal. The carrier signal is received within the ICS 14 and rectified to provide operating power for the ICS (which does not include its own independent power source). The data that modulates the carrier signal is stripped off of the carrier signal, demodulated, and is used to control the ICS. More particularly, the command signals (which represent one form of data) are received at the ICS and specify which of a multiplicity of electrode contacts within the electrode array 18 are to receive a stimulation current, the magnitude of the stimulation current, and the rate at which the stimulation current is applied. In this way, the user receives electrical stimulation in his or her cochlea for stimulating the auditory nerve going to the brain representative of the audio signals received by the external microphone 26. Thus, the user of the system 10 (a patient who is profoundly deaf and not able to otherwise hear normal audio sounds) is advantageously provided with the sensation of hearing.

Figure 1B:
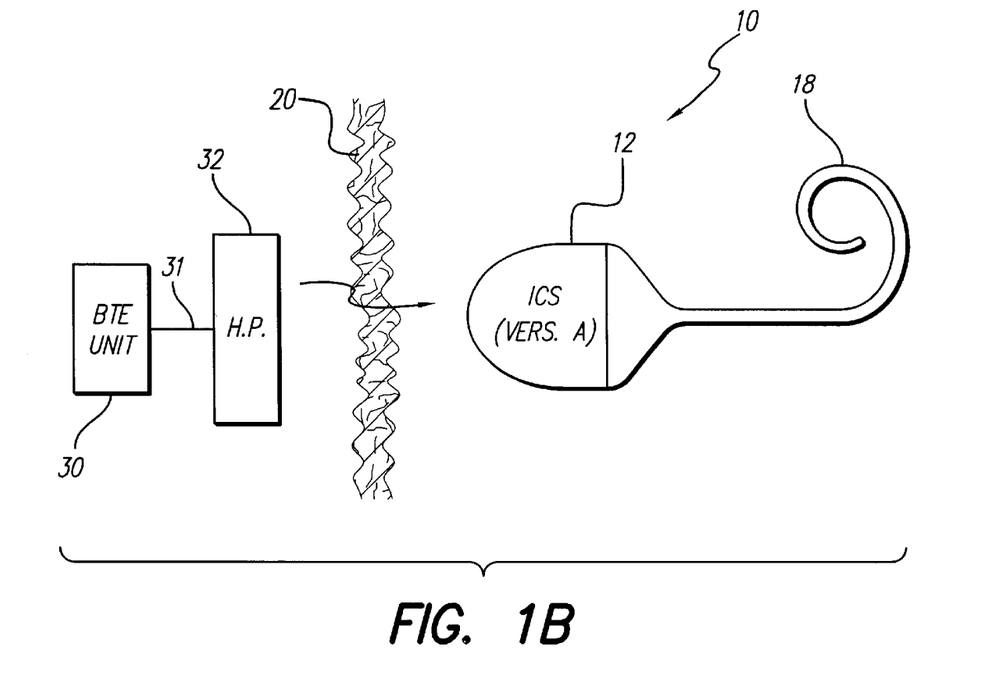
FIG. 1B schematically depicts the ICS of FIG. 1A coupled to an external behind-the-ear (BTE) unit.
Figure 1C:
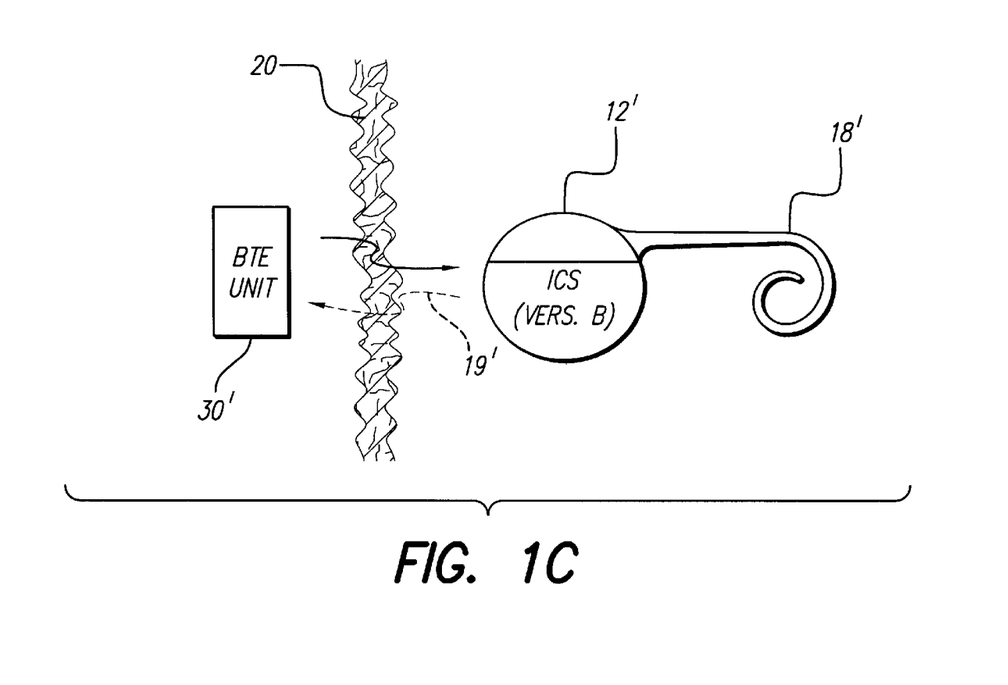
FIG. 1C schematically depicts a different version of an ICS coupled to the BTE unit of FIG. 1B.

Recent advances in the cochlea stimulation field have provided a small behind-the-ear (BTE) unit 30 that includes circuitry for carrying out essentially all of the functions previously performed by the WP 14. Typically, a HP 32 is connected to the BTE unit 30 via a short cable 31, as shown in FIG. 1B. In some embodiments, the BTE unit is designed to fit tightly against the scalp of the user. In such embodiment, the HP 32 may actually be included within a BTE unit 30', as shown in FIG. 1C. Regardless of the configuration of the BTE unit 30 (i.e., whether it uses a separate HP 32 or a built-in head piece), it must provide the necessary command signals to the ICS 12 to allow the ICS 12 to operate. For the embodiment illustrated in FIG. 1C, a new version of the ICS 12', denoted version "B", may be implanted in the patient. This version "B" ICS 12' may include different circuitry that does not generate a backtelemetry signal, or if it does, it generates a backtelemetry signal 19' based on different criteria than used with version "A".

In order for the BTE unit 30 to operate with the ICS 12, it must send the necessary command signals to the ICS 12 that enable it to operate. In the prior external circuitry, described above in connection with FIG. 1A, such command signals could not be sent until the backtelemetry handshake signal 19 had been received, indicating that the carrier signal was being received at the ICS, that sufficient power was present to enable operation of the iCS, and other status conditions were right for operation of the ICS. However, to include circuitry within the BTE unit 30 that receives and processes such a backtelemery handshake signal adds additional space and power consumption requirements to the design of the BTE unit 30 that are not compatible with its small space and low operating power requirements. Hence, it is a primary purpose of the present invention to provide circuitry within a small BTE unit, or other external transmitting circuitry, that does not require receipt of a backtelemery signal from an implanted receiver, e.g., an ICS 12, in order for the implanted receiver to operate. More particularly, it is a purpose of the present invention to provide detection circuitry within the external transmitter, e.g., within the BTE circuitry, that can detect the presence of the implanted ICS 12, and that can further detect whether or not the ICS 12 is aligned sufficiently with the external transmitter so as to properly receive its operating power, without having to receive and process an ICS-generated backtelemetry signal. A primary objective of such detection circuitry, given the limited space and power available within the BTE unit, is that the detection circuitry not occupy a very large volume, and that it not consume very much power.

Figure 2:
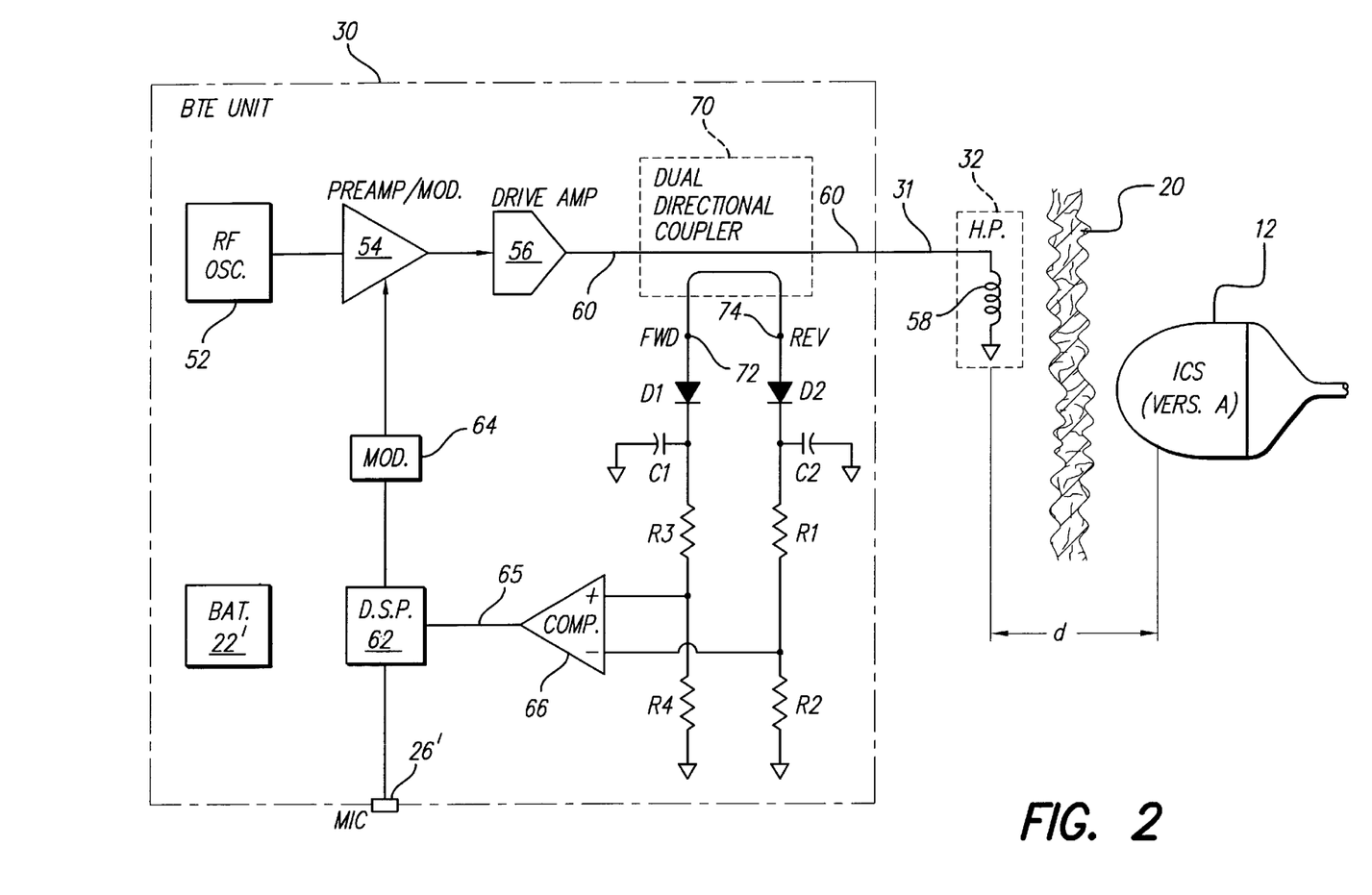
FIG. 2 shows a block diagram of an external transmitter usable with an implantable medical device, wherein the external transmitter includes circuitry for detecting whether a power link has been established with the implantable medical device without having to receive a back-telemetry carrier signal.

Turning next to FIG. 2, there is shown a block diagram of a BTE unit 30 usable with an implantable medical device, e.g., usable with the ICS 12, in accordance with the present invention. The circuitry within the BTE unit 30 advantageously detects whether a power link has been established with the implantable medical device, e.g., with the ICS 12, without having to receive a backtelemetry signal. The circuitry within the BTE unit 30 shown in FIG. 2 is ideally realized using very small components, consumes minimal power, and is therefore suitable for use within a small, light-weight external controller of the type that may be conveniently worn behind the ear of its user. Hence, the circuitry within the BTE unit 30 may hereafter be referred to as simply the BTE circuitry 30.

As seen in FIG. 2, the BTE circuitry 30 includes an RF oscillator 52 that generates an RF carrier signal. This RF carrier signal is amplified and modulated, as required, by a preamplifier/modulator circuit 54. The modulation applied to the carrier signal is derived from a digital signal processor (DSP) 62 and a modulator circuit 64, in conventional manner. The DSP 62, for example, implements a desired speech processing strategy and applies such strategy to audio signals sensed through a microphone 26'. As explained further below, the DSP 62 also receives a control signal, on signal line 65 (and hence, hereafter the control signal may be referred to as the control signal 65), from a comparator circuit 66. Such control signal 65 provides an indication as to whether or not a power link has been detected with the ICS 12. If the control signal 65 indicates that a power link has been detected with the ICS, then the DSP 62 is enabled to perform its desired function of generating the command signals needed for proper operation of the ICS 12. If, on the other hand, the control signal 65 indicates that a power link has not been detected with the ICS 12, then the DSP 62 is not enabled, and the command signals needed for operation of the ICS 12 are not generated nor sent to the ICS.

Also included within the BTE unit 30 is a battery 22' that provides the operating power for the entire system, i.e., for both the BTE circuitry 30 and the ICS 12. Because the batter 22' is included within the BTE unit, it must be small, light-weight, and readily replaceable; yet, in order to avoid the too-frequent replacement thereof (which would not only be expensive, but would be an annoyance for the user), the battery 22' must have sufficient energy storage capacity to operate the entire system for several hours. One type of battery that could be used for this purpose is disclosed in U.S. Pat. application Ser. No. 60/105,415, filed Oct. 23, 1998 (converted to a Non-Provisional application Ser. No. 09/200,398 on Nov. 24, 1998). More conventional batteries, sch as a lithium-ion battery, or a nickel methal-hydride (NiMH) battery, may also be used for the battery 22'.

Still with reference to FIG. 2, it is seen that the modulated carrier signal (i.e., the output from the preamplfier/modulator circuit 54), it is further amplified by drive amplifier 56, which drive amplifier 56 conditions the modulated carrier signal so that it is suitable for sending to the implanted ICS 12 through a coil 58 housd in a headpiece (HP) 32. The coil 58 is electrically connected to the drive amplifier 56 via an output power path 60. The output power path 60 includes the connection cable 31 that connects the HP 32 to the BTE circuitry 30. In accordance with the present invention, the output power path 60 also includes a dual direction coupler circuit 70. The coupler circuit 70 detects both forward power being sent to the ICS 12 over the output power path and reflected (or reverse) power returning on the output power path. When a good power link has been established with the ICS, the forward power remains approximately constant, regardless of the spacing "d"between the headpiece coil 58 and the implanted ICS. The detected reverse power, varies significantly as a function of the quality of the power link. Thus, by monitoring the reverse power, a good indication is provided of whether a power link has been established with the ICS 12. Thus, by monitoring the amount of reverse power, using comparator circuit 66, the BTE circuitry 30 is able to signal the DSP 62 when a sufficiently good power link exists for operation of the ICS 12.

A preferred technique for monitoring the reverse power is further illustrated in FIG. 2. As seen in FIG. 2, the directional coupler 70, in addition to the both an input and output port for connection to the output power path 60, includes a forward terminal 72 and a reverse terminal 74. The signal (typically a voltage signal) developed on the forward terminal 72 provides an indication of the amount of forward power being transmitted over the output power path. Similarly, the signal developed on the reverse terminal 74 provides an indication of the amount of reverse power being reflected from the load, where the "load" includes the headpiece coil 58 inductively coupled with the implanted ICS 12. Thus, by capturing the energy associated with the forward signal on capacitor C1 through diode D1, and by capturing the energy associated with the reverse signal on capacitor C2 through diode D2, the respective voltages held on capacitors C1 and C2 provide a measure of the forward and reverse power on the output power path 60, respectively. These voltages are then compared, using resistor-dividing networks R3–R4 and R1–R2. The signal appearing at the node of resistors R3 and R4 represents a threshold reference signal derived from the substantially constant forward power signal. The signal appearing at the node of resistors R1 and R2 represents a signal proportional to the varying or changing reverse power signal. When the reverse power signal exceeds the reference signal, then the output of the comparator circuit 66 changes, providing an indication that the power link status with the ICS 12 has also changed.

Figure 3:
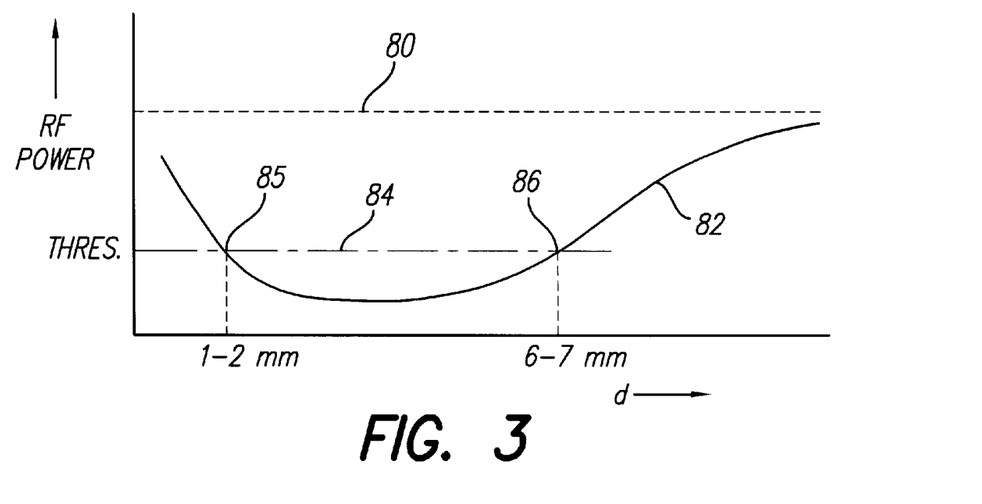
FIG. 3 is a graph that qualitatively depicts how the reflected power transmitted to an implantable medical device through a transmitting coil varies as a function of the separation distance between the transmitting coil and the implantable medical device.

The manner in which the forward and reverse power signals vary for a linked power condition, as a function of separation distance "d" between the headpiece coil 58 and the ICS 12, is qualitatively depicted in the graph shown in FIG. 3. In FIG. 3, the vertical axis represents the magnitude of the power present in both the forward (dashed line 80) and reverse (solid line 82) directions on the output power path. The horizontal axis represents the separation distance "d". As seen in FIG. 3, the forward power remains relatively constant over a large distance "d". The reverse power, on the other hand, dips significantly between a separation distance of about 1–2 mm and 7–8 mm. Thus, what the BTE circuitry 30 does is to set a threshold value, line 84, that intersects with the reverse power line 82 at two points, points 85 and 86. So long as the reverse power remains below the threshold value, i.e., so long as the detected reverse power resides between points 85 and 86, then that provides a good indication that a valid power link condition exists. However, should the reverse power exceed the threshold 84, then that provides an indication that a valid power link condition does not exist.

Accordingly, when the comparator circuit 66 detects that a valid link condition does not exist, then the control signal 65 changes. A change in the control signal 65, in turn, signals the DSP 62 that some type of appropriate corrective action is needed. Such action may include, e.g., resending an initialization command sequence to the ICS, and/or triggering some sort of alarm that the user can sense (so that he or she can reposition the HP 32, or take other action).

Figure 4:
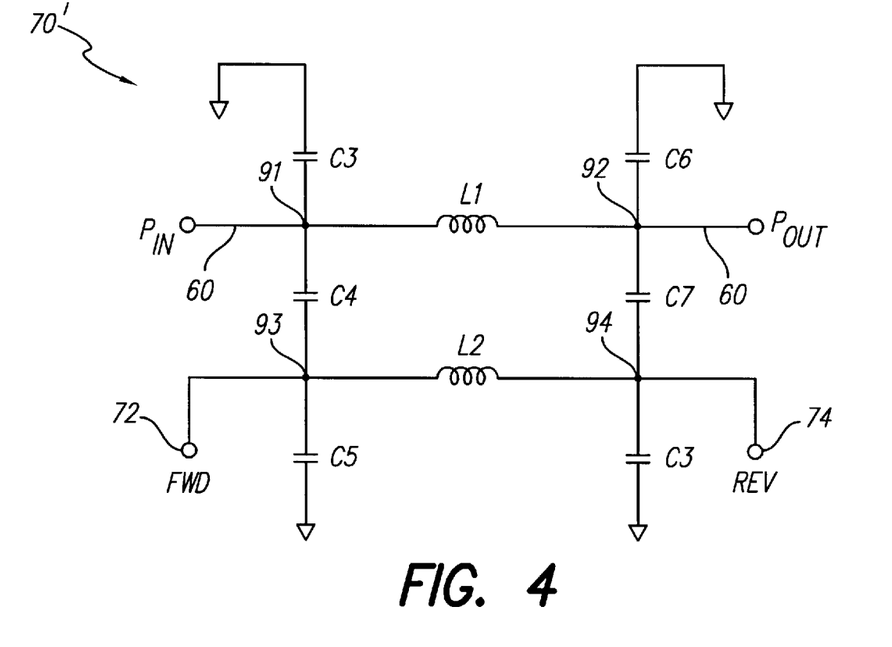
FIG. 4 is a schematic diagram of one type of dual directional coupler that may be used within the external transmitter of FIG. 2.

Turning next to FIG. 4, a schematic diagram of one type of dual directional coupler circuit 70' that may be used within the BTE circuit 30 is illustrated. As seen in FIG. 4, the dual directional coupler circuit 70' comprises a circuit having a first node 91, a second node 92, a third node 93 and fourth node 94. The first node 91 is connected to an input power terminal $P_{IN}$, a capacitor C3 connected to ground, an inductor L1 connected to the second node 92, and a capacitor C4 connected to the third node 93. The second node 92 is connected to an output power terminal $P_{OUT}$, a capacitor C6 connected to ground, the inductor L1 connected to the first node 91, and a capacitor C7 connected to the fourth node 94. The third node 93 is connected to the forward power port 72, a capacitor C5 connected to ground, an inductor L2 connected to the fourth node 94, and the capacitor C4 connected to the first node 91. The fourth node 94 is connected to the reflected or reverse power port 74, a capacitor C8 connected to ground, the inductor L2 connected to the third node 93, and the capacitor C7 connected to the second node 92. The first node 91 and the second node 92 are connected in-line with the output power path 60.

For a carrier signal on the output power path having a frequency of approximately 49 MHz, representative values of the discrete components shown in FIG. 4 are as follows: C3=C6=56 pF; C4=C7=5.6 pF; C5=C8=68 pF; and L1=L2= 150 $\mu$h. With such circuit, the diodes D1 and D2 (FIG. 2) may be realized with 1N5712 RF signal diodes, available from numerous semiconductor manufacturers. The capacitors C1 and C2 may be about 1000 pF, and the resistors R3 and R4 are selected to provide a threshold reference voltage at the "+" input of the comparator circuit 66 of approximately 20–30 mV. Similarly, the resistors R1 and R2 are selected to provide a signal level at the "−" input of the comparator circuit 66 that is less than 20–30 mV for a separation distance "d" between the points 85 and 86.

Figure 5:
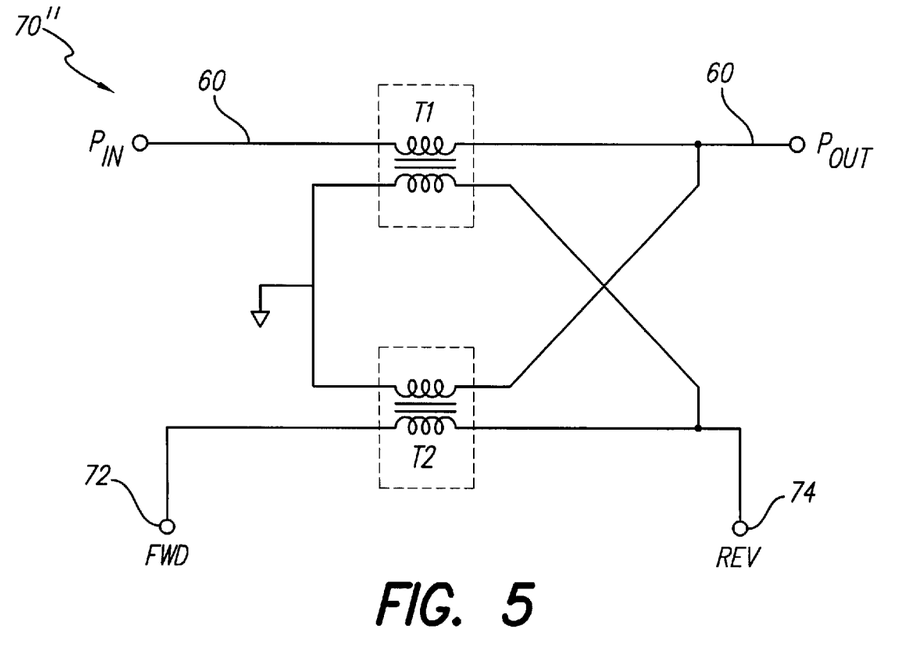
FIG. 5 is a schematic diagram of another type of dual directional coupler that may be used within the external transmitter of FIG. 2.

FIG. 5 is a schematic diagram of another type of dual directional coupler circuit 70" that may be used within the BTE circuit 30. The circuit shown in FIG. 5 uses two transformers, T1 and T2, each having a respective primary and secondary winding wound on a magnetic toroid core. As seen in FIG. 5, a first end of the primary winding of transformer T1 is connected to an input power terminal $P_{IN}$, and the second end of the primary winding of transformer T1 is connected to an output power terminal, $P_{OUT}$. A first end of the secondary winding of the transformer T1 is connected to ground, and a second end of the secondary winding of the transformer T1 is connected to the reflected power port 74. A first end of the primary winding of the transformer T2 is connected to the forward power port 72. The second end of the primary winding of the transformer T2 is connected to the reflected power port 74. A first end of the secondary winding of the transformer T2 is connected to ground. A second end of the secondary winding of the transformer T2 is connected to the output power terminal $P_{OUT}$. In use, the input power terminal $P_{IN}$ and the output power terminal $P_{OUT}$ are connected in-line with the output power path 60.

It should also be noted that other types of dual directional coupling circuits, in addition to those shown in FIGS. 4 and 5, may be used with the invention. For example, directional coupler circuits made with strip lines closely spaced together, as are known in the art, could be used as the directional coupler 70.

A significant feature of the invention is that the circuitry components for whatever type of dual directional coupler circuit is used are passive components, thereby consuming minimal power, and may be very small, thereby using very little space within the BTE. Embodiments of the dual directional coupler circuit 70 built to date consume less than about 1 mW of power and occupy a volume less than about 1×1×0.5 cm$^3$.

Figure 6:
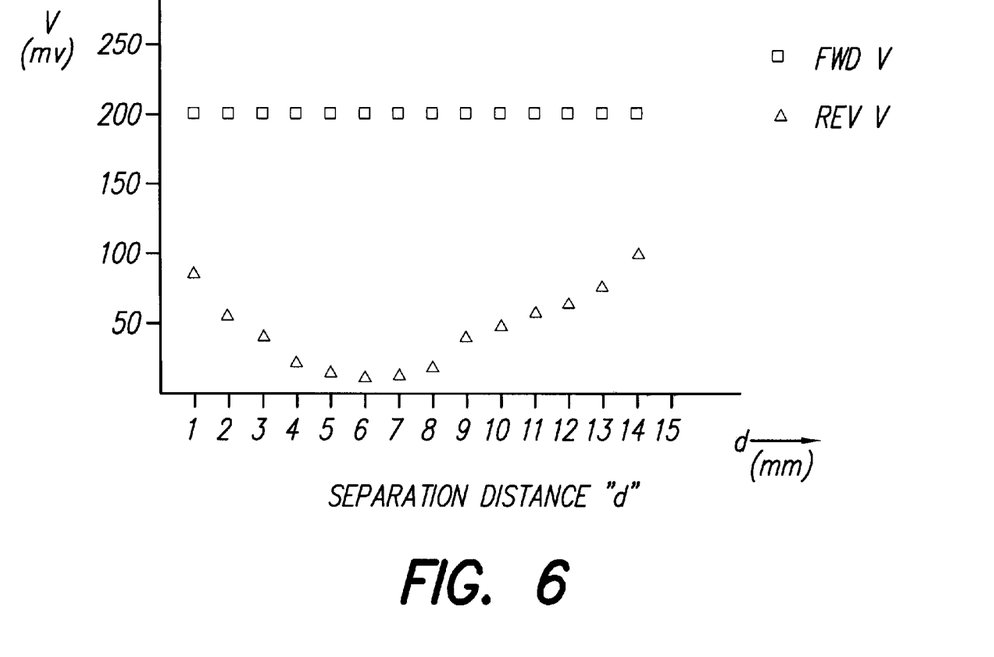
FIG. 6 is a graph of quantitative data that depicts forward and reverse voltage as a function of separation distance, and further helps illustrate operation of the invention.

Turning next to FIG. 6, there is shown a graph of quantitative data using a coupler circuit of the type illustrated in FIG. 4. As seen in FIG. 4, the forward voltage, $V_{FWD}$, which is directly proportional to the forward power, is approximately constant over a separation distance of about 14 mm. In contrast, the reverse voltage, $V_{REV}$, over the same separation distance drops to as low as approximately 10 mV between a separation distance "d" of about 4 to 7 mm, and raises to as high as about 80 mV at a separation distance "d" of about 1 mm, and 60–70 mV at a separation distance "d" of about 11–13 mm. Thus, by setting the threshold reference to a value of between about 20–40 mV, it is possible to clearly detect when the reverse voltage $V_{REV}$ exceeds this reference level, and thus provide an indication of when a valid power link between the BTE circuit and the ICS is present and when it is not.

As described above, it is thus seen that the present invention provides a method and apparatus for detecting when a valid power link condition exists between a transmitting circuit and a receiving circuit without the need for back-telemetry signals from the receiving circuit. Further, it is seen that the invention provides power-link detection circuitry that consumes very little power, e.g., much less than about 1 mW, is very small, and is thus highly suitable for use in small, light-weight, battery-operated BTE cochlea-stimulation systems.

While the invention herein disclosed has been described by means of specific embodiments and applications thereof, numerous modifications and variations could be made thereto by those skilled in the art without departing from the scope of the invention set forth in the claims.

What is claimed is:

1. Transmitting apparatus usable for transmitting power to an implantable medical device that determines whether a power link has been established with the implantable medical device, comprising:

an RF oscillator that generates an RF signal;
   a headpiece having a transmitting coil;
   a power amplifier that amplifies the RF signal to produce an RF power signal;
   an output power path that connects the RF power signal with the transmitting coil;
   a directional coupler connected in-line with the output power path between the power amplifier and the transmitting coil, the directional coupler having a reflected power port on which a reflected power signal appears having a magnitude proportional to reflected power present on the output power path; and
   a comparator circuit that compares the reflected power signal to a threshold reference signal and that generates a power link status signal as a function of whether the reflected power signal exceeds the threshold reference signal;
   wherein the power link status signal provides a LINK or NO-LINK indication of whether a power link is established with the implantable medical device.

2. The transmitting apparatus of claim 1 wherein the directional coupler comprises a dual directional coupler that also has a forward power port on which a forward power signal appears having a magnitude proportional to the forward power present on the output power path, and wherein the threshold reference signal is derived form the forward power signal.

3. The transmitting apparatus of claim 2 wherein the dual directional coupler comprises a circuit having a first, second, third and fourth node;

the first node being connected to an input power terminal, a first capacitor (C3) connected to ground, a first inductor (L1) connected to the second node, and a second capacitor (C4) connected to the third node;
   the second node being connected to an output power terminal, a third capacitor (C6) connected to ground, the first inductor (L1) connected to the first node, and a fourth capacitor (C7) connected to the fourth node;
   the third node being connected to the forward power port, a fifth capacitor (C5) connected to ground, a second inductor (L2) connected to the fourth node, and the second capacitor (C4) connected to the first node; and
   the fourth node being connected to the reflected power port, a sixth capacitor (C8) connected to ground, the second inductor (L2) connected to the third node, and the fourth capacitor (C7) connected to the second node;
   wherein the first and second nodes are connected in-line with the output power path.

4. The transmitting apparatus of claim 2 wherein the dual directional coupler comprises a circuit having first and second transformers, each transformer having a respective primary and secondary winding wound on a magnetic toroid core, wherein a first end of the primary winding of the first transformer is connected to an input power terminal, and the second end of the primary winding of the first transformer is connected to an output power terminal;
   a first end of the secondary winding of the first transformer is connected to ground, and a second end of the secondary winding of the first transformer is connected to the reflected power port;
   a first end of the primary winding of the second transformer is connected to the forward power port, and the second end of the primary winding of the second transformer is connected to reflected power port; and
   a first end of the secondary winding of the second transformer is connected to ground, and a second end of the secondary winding of the second transformer is connected to the output power terminal;
   wherein the input power terminal and the output power terminal are connected in-line with the output power path.

5. The transmitting apparatus of claim 1 further including digital signal processing (DSP) means for generating control signals for controlling the implantable medical device, and modulation means for modulating the RF signal with the control signals, whereby the control signals are transmitted to the implantable medical device.

6. The transmitting apparatus of claim 5 wherein the power link status signal is connected to the DSP means, and wherein the DSP means includes means for detecting a change in the power link status signal, and for further responding to a power link status signal change from a NO-LINK to a LINK condition that automatically generates an initialization command sequence that is transmitted to the implantable medical device.

7. The transmitting apparatus of claim 6 wherein the DSP means includes means for responding to a change from a LINK to a NO-LINK condition by generating an alarm signal that notifies a user of the transmitting apparatus of the changed status.

8. The transmitting apparatus of claim 1 wherein the RF signal generated by the RF oscillator comprises an RF signal having a frequency of approximately 49 MHz.

9. The transmitting apparatus of claim 8 wherein the implantable medical device comprises an implantable cochlear stimulator (ICS).

10. The transmitting apparatus of claim 9 wherein the elements of the transmitting apparatus are packaged within a small, light-weight housing adaptable to be worn behind the ear of a user.

11. Apparatus that determines whether a power link is established with an implantable medical device, comprising:

means generating a power signal;
    a transmitter that transmits the power signal to the implantable medical device over an output power path;
    means for monitoring reflected power present on the output power path;
    comparison means for comparing the reflected power to a threshold reference signal; and
    means for generating a power link status signal as a function of the comparison to the threshold reference signal.

12. The apparatus of claim 11 further including means for monitoring the forward power present on the output power path, and means for deriving the threshold reference signal from the monitored forward power.

13. The apparatus of claim 12 wherein the means for monitoring the forward power present on the output power path comprises a directional coupler.

14. The apparatus of claim 13 wherein the directional coupler comprises a circuit having a first, second, third and fourth node, and wherein:

the first node is connected to an input power terminal, a first capacitor (C3) is connected to ground, a first inductor (L1) is connected to the second node, and a second capacitor (C4) is connected to the third node;

the second node is connected to an output power terminal, a third capacitor (C6) is connected to ground, the first inductor (L1) is connected to the first node, and a fourth capacitor (C7) is connected to the fourth node;

the third node is connected to the forward power port, a fifth capacitor (C5) is connected to ground, a second inductor (L2) is connected to the fourth node, and the second capacitor (C4) is connected to the first node; and the fourth node is connected to a reflected power port, a sixth capacitor (C8) connected to ground, the second inductor (L2) is connected to the third node, and the fourth capacitor (C7) is connected to the second node; and the first and second nodes are connected in-line with the output power path.

15. A method of determining whether a power link is established with an implantable medical device, comprising the steps of:

(a) generating a power signal;

(b) transmitting the power signal to the implantable medical device over an output power path;

(c) monitoring reflected power present on the output power path;

(d) comparing the reflected power to a threshold reference signal; and (e) generating a power link status signal as a function of the comparison performed in step (d).

16. The method of claim 15 further including monitoring the forward power present on the output power path, and deriving the threshold reference signal from the monitored forward power.

* * * * *